United States Patent [19]

Giordano et al.

[11] Patent Number: 4,973,696

[45] Date of Patent: Nov. 27, 1990

[54] STEREOSELECTIVE PROCESS FOR PREPARING OPTICALLY ACTIVE ALPHA, BETA-DISUBSTITUTED CARBONYL COMPOUNDS

[75] Inventors: Claudio Giordano, Monza; Graziano Castaldi, Briona; Silvia Cavicchioli, Costermano; Francesco Minisci, Milan, all of Italy

[73] Assignee: Zambon S.p.A., Vicenza, Italy

[21] Appl. No.: 297,387

[22] Filed: Jan. 17, 1989

Related U.S. Application Data

[63] Continuation-in-part of Ser. No. 940,611, Dec. 11, 1986, abandoned.

[30] Foreign Application Priority Data

Dec. 13, 1985 [IT] Italy ............................... 23216 A/85

[51] Int. Cl.$^5$ ............................................ C07D 317/34

[52] U.S. Cl. ................................... 546/267; 549/60; 549/73; 549/267; 549/274; 549/473; 549/483; 549/498; 548/517; 548/518; 548/562; 568/319; 568/386; 568/397; 568/435; 568/483; 546/174; 546/315; 546/284; 546/283; 546/281; 546/275

[58] Field of Search ............... 568/319, 386, 397, 435, 568/483; 546/267, 275, 281, 283, 284, 315, 174; 549/60, 73, 473, 483, 498; 548/517, 518, 562

[56] References Cited

U.S. PATENT DOCUMENTS 4,764,641 8/1988 Castaldi et al. ..................... 568/483
4,764,692 8/1988 Castaldi et al. ..................... 563/319

*Primary Examiner*—Robert T. Bond
*Attorney, Agent, or Firm*—Cushman, Darby & Cushman

[57] ABSTRACT

A stereoselective process is described for preparing optically active alpha,beta-disubstituted carbonyl compounds, comprising forming an acetal between an alpha,beta-unsaturated aldehyde or ketone and tartaric acid or a derivative thereof, halogenating the product thus obtained, and restoring the carbonyl compound.

5 Claims, No Drawings

STEREOSELECTIVE PROCESS FOR PREPARING OPTICALLY ACTIVE ALPHA, BETA-DISUBSTITUTED CARBONYL COMPOUNDS

This invention relates to a process for the stereoselective functionalisation of alpha, beta-unsaturated carbonyl compounds. The process comprises forming an acetal between an alpha, beta-unsaturated aldehyde or ketone and L(+) or D (−)-tartaric acid or their derivatives, halogenating the resultant product to obtain an optically active halohydrin or dihalo derivative, and restoring the carbonyl function.

More particularly, the present invention relates to a process for preparing compounds of formula

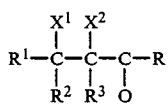 (I)

in which

R represents a hydrogen atom, an optionally substituted alkyl, an optionally substituted phenyl or a benzyl;

$R^1$, $R^2$ and $R^3$, which can be the same or different, represent a hydrogen atom, an optionally substituted alkyl or an optionally substituted aryl;

one of $X^1$ and $X^2$ represents a chlorine, bromine or iodine atom, and the other represents an optionally protected hydroxy or a chlorine, bromine or iodine atom.

Of the meanings of the radicals $R^1$, $R^2$ and $R^3$, "optionally substituted alkyl" preferably means a $C_1$-$C_4$ alkyl optionally substituted with from one to three substituents chosen from halogen atoms, hydroxy, nitro, cyano, $C_1$-$C_4$ alkoxy or $C_3$-$C_6$ cycloalkyl groups, aromatic groups such as phenyl, naphthyl, pyridyl, furyl or thienyl which can themselves be substituted with halogen atoms, $C_1$-$C_4$ alkyl or alkoxy groups; "optionally substituted aryl" means an aromatic or heteroaromatic group having 5,6,10 or 12 atoms such as furyl, thienyl, pyrrolyl, phenyl, pyridyl, naphthyl, quinolyl or diphenyl, said aromatic groups being optionally substituted with from one to three substituents chosen from halogen atoms, hydroxy, $C_1$-$C_4$ alkyl, $C_1$-$C_4$ alkylthio, $C_1$-$C_4$ alkoxy, cyano, nitro, $C_1$-$C_4$ acyloxy, $C_1$-$C_4$ haloalkyl or $C_1$-$C_4$ haloalkoxy groups. If $R^1$ is equal to $R^2$ in the compounds of formula I, these allow the existence of two enantiomers.

By means of the process according to the present invention it is possible to prepare the desired enantiomer in a highly enantioselective manner.

If $R^1$ is different form $R^2$ in the compounds of formula I, these comprise at least two asymmetric centres (the carbon atoms to which the substituents $X^1$ and $X^2$ are bonded) and therefore allow the existence of four stereoisomers.

By means of the process according to the present invention it is possible to obtain the preponderant and in many cases exclusive formation of the desired stereoisomer.

The first stage of the process comprises the preparation, in the manner described hereinafter, of a compound of formula

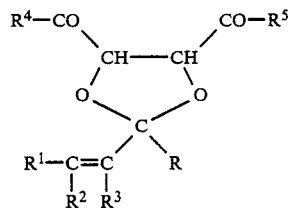

in which

R, $R^1$, $R^2$ and $R^3$ have the aforesaid meanings:

$R^4$ and $R^5$, which can be the same or different, represent a hydroxy, an alkoxy, an amino, mono or dialkylamino, 1-pyrrolidyl or 1-piperidyl group, or an $O^-M^+$ represents the cation of an alkaline metal;

the carbon atoms marked with an asterisk both have R configuration if compound II derives form L(+)-tartaric acid, or both have S configuration if compound II derives form D(−)-tartaric acid. The compounds of formula II are prepared form aldehydes of ketones of formula

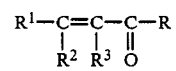 (III)

(in which R, $R^1$, $R^2$ and $R^3$ have the aforesaid meanings). The aldehyde (R=H) or the ketone of formula III is condensed with L(+) or D(−)-tartaric acid or their derivatives.

The reaction is a normal acetalization reaction which is conducted in an inert solvent, either in the presence of a dehydrating agent such as a trialkylorthoformate or by azeotropic distillation of the water of reaction, or again by transacetalization using for example a tartaric acid acetonide.

Tartaric acid diesters are preferably used, leading to the formation of compounds of formula II in which $R^4$ and $R^5$ are alkoxy. The other derivatives are obtained from these by simple amidation, hydrolysis or salification.

The second stage of the process comprises stereoselective halogenation of a compound of formula II with a suitable halogenating agent in a suitable solvent. The third stage of the process then follows, consisting of the transformation of the halogenation product, leading to the compound I or its immediate precursors such as the corresponding alcohols and ethers or their derivatives.

Suitable halogenating agents are N-bromo-succinimide, N-bromo-acetamide, N-chloro-succinimide, N-iodo-succinimide, N-haloamines in general, cupric bromide, hexachloro-cyclohexadienone, bromine optionally in the presence of buffer solutions alkyl or alkaline hypochlorites, iodine, iodine chloride, tetra-alkylammonium or tetra-alkylphosphonium perhalides, etc. The use of bromine, chlorine or iodine can lead to the formation of dihalo derivatives of formula I ($X^1$ and $X^2$=halogen) after hydrolysis. Suitable solvents are halogenated hydrocarbons such as $CHCl_2$ $CH_2Cl_2$, $CH_2Cl—CH_2Cl$, $CHCl_2—CH_3$, $CCl_4$, acetonitrile, dimethylformamide, formamide, acetamide, dimethylacetamide, tetrahydrofuran, dioxane, methanol, ethanol, ethyl ether, water or their mixtures, etc. Preferred solvents are mixtures of non-nucleophilic and nucleophilic solvents, particularly preferred solvents being nonprotic polar solvents in the presence of a polar solvent such as water.

The third stage of the process, i.e. transformation of the halogenated compounds to obtain the compounds I, is effected by various methods, for example by hydrolysis in a acidic medium.

An intermediate having a different structure which depends on the specific compound of formula II used can be isolated from the second process stage, i.e. after halogenating compound II.

For example, halogenation of the compounds of formula II leads in certain cases to an isolable intermediate of formula

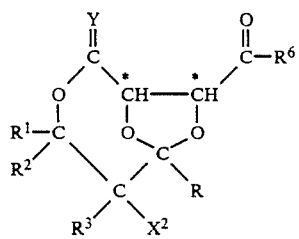

or

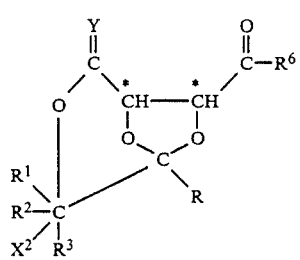

in which R, $R^1$, $R^2$ and $R^3$ have the aforesaid meanings; $R^6$ has the meanings given for $R^4$, or is a

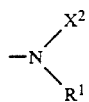

group;

$X^2$ represents a chlorine, bromine or iodine atom;

Y represents an oxygen atom or an =N—$R^7$ group in which $R^7$ represents a hydrogen, chlorine, bromine or iodine atom, an optionally substituted alkyl or an optionally substituted aryl.

Hydrolysis of compound IVa or IVb then leads to the aldehyde or ketone I of formula:

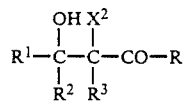

or, respectively, of formula

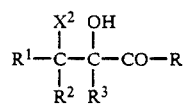

As the tartaric derivative is recovered unaltered after the hydrolysis step and can be reused for other preparations, the process according to the present invention is equivalent to transforming an alpha, beta-unsaturated carbonyl compound into an alpha, beta-disubstituted carbonyl compound with high stereoselectivity.

As stated heretofore, the special characteristic of the process according to the present invention is that it enables compounds of formula I to be obtained in optically active form with high yield and high optical purity.

If the compounds of formula I comprise two asymmetric centres namely the carbon atoms in the alpha and beta position to the carbonyl (indicated hereinafter as $C_a$ and $C_b$ respectively), they allow the existence of four stereoisomers.

The process according to the present invention enables one of the four stereoisomers to be selectively obtained by directing the synthesis a priori towards the desired stereoisomer.

The parameters which can be varied to selectively obtain the desired stereoisomer are the geometry (E or Z) of the unsaturated starting compound (compound III), and the isomerism of the tartaric derivative used in the preparation of compound II. The same two parameters enable the synthesis to be directed towards the desired enantiomer if $R^1$ is equal to $R^2$ in the unsaturated starting compound.

The following example relating to aldehydes of the

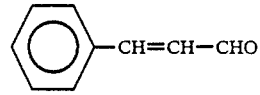

type will clarify this concept.

Starting from the E isomer and preparing by way of a tartaric acid derivative the corresponding compound of formula II, then subjecting this to bromination and hydrolysis, the aldehyde of formula

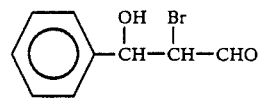

is obtained in which the centres of asymmetry Ca and Cb both have R or S configuration.

Selection of the RR or SS stereoisomer depends on the tartaric derivatives [L(+) or D(−)] used in forming the compound II. Stereoselectivity towards a specific stereoisomer is generally very high, and an excess of the desired stereoisomer exceeding 90% can often be obtained. This result, combined with high chemical yield, makes the process according to the present invention particularly important for preparing all those compounds of formula I which are used in optically active form.

Thus, for example, the bromination with N-bromosuccinimide of the acetal obtained from (E)-cinnamic aldehyde and di-N,N-dimethylamide of L(+)-tartaric acid affords, after hydrolysis with methanol, the N,N-dimethylamide of 2-[1(S)-bromo-2-(S)-hydroxy-2-phenylethyl]-1,3-dioxolane-4(R)-methoxycarbonyl-5(R)-carboxylic acid.

The expert of the art will understand the importance of the process according to the invention in providing single-enantiomer compounds of formula I as extremely useful and versatile intermediates in the preparation of numerous optically active compounds by just a few simple transformations. These transformations include the preparation of optically active epoxides, which when opened lead to the formation of other optically active functionalised derivatives; substitution of the halogen atom (substituent $X^1$ or $X^2$ in formula I) by nucleophilic groups such as the amino group; transformation of the aldehyde or ketone group, etc.

Transformation of the $X^1$ and $X^2$ groups can obviously be carried out before the hydrolysis step, i.e. directly on the product deriving from the halogenation of compound II.

By means of these reactions or analogous transformation, optically active compounds of pharmaceutical interest or their precursors can be prepared.

Such compounds comprise amino acids such as phenylalanine ($R^1$=phenyl), tyrosine ($R^1$=4-hydroxy-phenyl), m.tyrosine ($R^1$=3-hydroxy-phenyl), adrenergic medicaments such as metaraminol ($R^1$=3-hidroxy-phenyl), anticholinergic medicaments such as DOPA ($R^1$=3,4-dihydroxy-phenyl), antibiotics or their precursors such as chloramphenicol ($R^1$=4-nitro-phenyl), thiamphenicol ($R^1$=4-methylsulphonyl-phenyl) or the reduced intermediate ($R^1$=4-methylthio-phenyl), anti-inflammatory medicaments such as naproxen (R=6-methoxy-2-naphtyl, $R^1$=H) or the optically active compound 2,3-epoxy-1-propanol ($R^1$=$R^2$=$R^3$=H), which is a useful intermediate in the preparation of medicaments such as carnitine, penbutolol and 1-moprolol, and 2,3-epoxy-cinnamic acid which is an intermediate for the preparation of the drug known as Dilthiazem.

A typical embodiment of the stereoselective process for preparing optically active alpha, beta-difunctionalised carbonyl compounds following the present invention comprises (a) reacting an alpha,beta-unsaturated aldehyde or ketone of formula

(III)

wherein

R represents a hydrogen atom; a $C_1$-$C_4$ alkyl group optionally substituted with from one to three substituents chosen from halogen atoms, hydroxy, nitro, cyano, $C_1$-$C_4$ alkoxy or or $C_3$-$C_6$ cycloalkyl groups, phenyl, naphthyl, pyridyl, furyl or thienyl which can themselves be substituted with halogen atoms, $C_1$-$C_4$ alkyl or alkoxy groups; a benzyl or a phenyl group optionally substituted with from one to three substituents chosen from halogen atoms, hydroxy, nitro, cyano, $C_1$-$C_4$ alkyl, $C_1$-$C_4$ alkylthio, $C_1$-$C_4$ alkoxy, $C_1$-$C_4$ acyloxy, $C_1$-$C_4$ haloalkyl or $C_1$-$C_4$ haloalkoxy groups;

$R^1$, $R^2$ and $R^3$, which can be the same or different, represent a hydrogen atom; a $C_1$-$C_4$ alkyl group optionally substituted with from one to three substituents chosen from halogen atoms, hydroxy, nitro, cyano, $C_1$-$C_4$ alkoxy or or $C_3$-$C_6$ cycloalkyl groups, phenyl, naphtyl, pyridyl, furyl or thienyl which can themselves be substituted with halogen atoms, $C_1$-$C_4$ alkyl or alkoxy groups; an aryl group chosen from furyl, thienyl, pyrrolyl, phenyl, pyridyl, naphtyl, quinolyl or diphenyl, said groups being optionally substituted with from one to three substituents chosen from halogen atoms, hydroxy, nitro, cyano, $C_1$-$C_4$ alkyl, $C_1$-$C_4$ alkylthio, $C_1$-$C_4$ alkoxy, $C_1$-$C_4$ acyloxy, $C_1$-$C_4$ haloalkyl or $C_1$-$C_4$ haloalkoxy groups; with L(+) tartaric acid or D (−) tartaric acid or a derivative thereof of formula $R^4$—CO—CH(OH)—CH(OH)—CO—$R^5$ wherein $R^4$ and $R^5$, which can be the same or different, represent hydroxy, $C_1$-$C_4$ alkoxy or an amino group mono- or di-substituted with $C_1$-$C_4$ alkyl, 1-pyrrolidyl or 1-piperidyl group, or an $O^-M^+$ group where $M^+$ represents the cation of an alkaline metal; in an inert solvent, in the presence of an acid catalyst at a temperature of from room up to reflux temperature, for a period of time of from 2 to 20 hours, by eliminating the reaction water by means of a dehydrating agent or by azeotropic distillation;

(b) halogenating the obtained ketal of formula

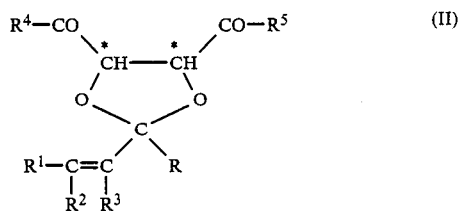

(II)

in which R, $R^1$, $R^2$, $R^3$, $R^4$ and $R^5$ have the same meanings as above, at a temperature of from −10° C. to 20° C., for a period of time of from 1 to 48 hours, in a solvent chosen from halogenated hydrocarbon, acetonitrile, ethyl ether, amides, aliphatic alcohols, tetrahydrofuran, dioxane, water or their mixtures, by means of an halogenating agent chosen from chlorine, bromine, iodine, iodine chloride, tetra-alkylammonium or tetra-alkylphosphonium perhalides, N-bromo-succinimide, N-bromo-acetamide, N-chloro succinimide, N-iodo-succinimide, N-halo-amines, cupric bromide, hexachloro-cyclohexadienone;

(c) hydrolysing the obtained compound of formula

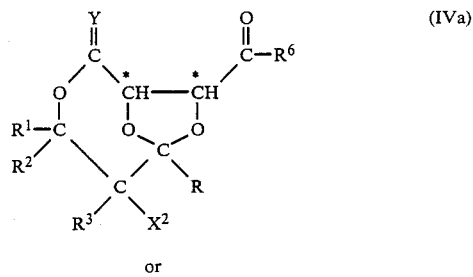

(IVa)

or

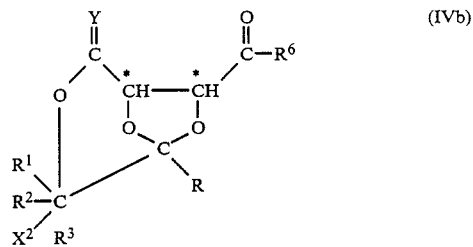

(IVb)

in which

R, $R^1$, $R^2$, $R^3$, $R^4$ have the same meanings as above and $R^6$ has the meanings given for $R^4$, or is a —N($X^2R^1$);

$X^2$ represents a chlorine, bromine or iodine atom;

Y represents an oxygen atom or an =N—$R^7$ group in which $R^7$ represents a hydrogen, chlorine, bromine or iodine atom, a $C_1$-$C_4$ alkyl, or a phenyl;

at a temperature of from room temperature to 100° C. in an alcoholic or aqueous/alcoholic medium, for a period of time of from 2 to 20 hours, to an aldehyde or to a ketone of formula

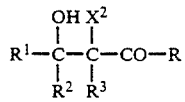

(Ia)

or

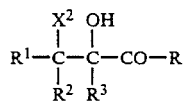

(Ib)

in which R, $R^1$, $R^2$, $R^3$, and $X^2$ have the same meanings as above.

The following examples are given to better illustrate the invention.

EXAMPLE 1

Preparation of the dimethyl ester of (E)-2-(2-phenyl-ethenyl)-1,3-dioxolane-4(R),5(R)-dicarboxylic acid

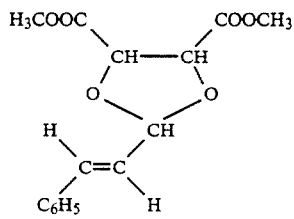

A solution of E-cinnamaldehyde (95,23 g; 0.75 mol), trimethylorthoformate (115.22 ml; 111.2 g; 1.05 mol), methanol (43 ml; 34 g; 1.05 mol), dimethyl ester of 2(R), 3(R) -dihydroxy-butanedioic acid (187.04 g; 1.05 mol) and methanesulphonic acid (4.8 ml; 7.10 g; 0.075 mol) is kept at 40° C. for 30 minutes.

While maintaining the temperature at 40° C., the low-boiling components are distilled off under vacuum (about 14 mmHg). At the end of the reaction, the mixture is poured into a 10% sodium bicarbonate solution and extracted with dichloromethane.

The combined organic extracts are washed with water and dried with sodium sulphate. Evaporation of the solvent under vacuum leaves a residue which is purified by chromatography ($SiO_2$; eluent; dichloromethane) to give the dimethyl ester of (E)-2-(2-phenyl-ethenyl)-1,3-dioxolane-4(R),5(R)-dicarboxylic acid (175 g; 0.60 mol yield 80%) as an oil.

$^1$H-NMR (90 MHz, $CDCl_3$-TMS) delta (ppm); 3.80 (s, 6H); 4.85 (ABq, 2H, J=3.6 Hz, Δv=8.90 Hz); 5.8 (d, 1H, $J_{AB}$=6.6 Hz); 6.23 (dd, 1H, $J_{AB}$=6.6 Hz, $J_{BX}$=15.6 Hz); 6.87 (d, 1H, $J_{BX}$=15.6 Hz); 7.26-7.57 (aromatic protons, 5H).

I.R. (Neat) $cm^{-1}$: 1760 (C=O).
$[\alpha]_D^{20}$=+10.05°(C=1, chloroform).

EXAMPLE 2

Preparation of the di-N,N-dimethylamide of .(E)-2-(2-phenyl-ethenyl)-1,3-dioxolane-4(R),5(R) -dicarboxylic acid A mixture of the dimethylester of (E)-2-(2-phenyl-ethenyl)-1,3-dioxolane-4(R),5(R)-dicarboxylic acid (29.29 g; 0.1 mol) and a 40% aqueous solution of dimethylamine (134 ml) is kept under stirring at room temperature for 4 hours. Decolorising charcoal is added to the reaction mixture, which is then filtered through celite. The solution obtained in this manner is concentrated under vacuum (about 14 mmHg) at 35°-40° C. until the excess dimethylamine has completely evaporated. The aqueous solution is then extracted with 1,2-dichloroethane. The combined organic extracts are dried with sodium sulphate. Evaporation of the solvent under vacuum leaves a residue which is purified by chromatography ($SiO_2$; eluent dichloromethane; ethyl acetate =8:2). A solid residue is obtained which by suspension in ethyl ether provides the di-N,N-dimethylamide of (E)-2-(2-phenyl-ethenyl)-1,3-dioxolane-4(E),5(R)-dicarboxylic acid (6.38 g; 0.02 mol yield 20%). M.p. 121°-123° C.

$^1$H-NMR (90 MHz, $CDCl_3$-TMS) delta (ppm); 2.96 (s, 6H); 3.16 (s, 6H); 5.33 (ABq, J=6 Hz, Δv=6.71 Hz); 5.70 (d, 1H, $J_{AB}$=6.6 Hz); 6.16 (dd, 1H, $J_{AB}$=6.6 Hz, $J_{BX}$=15.6 Hz); 6.8 (d, 1H, $J_{BX}$15.6 Hz); 7.23-7.47 (m, 5H, aromatic protons).

I.R. (Nujol Mull; stretching C=0 1640 $cm^{-1}$
$[\alpha]_D^{20}$=-28.43° (C=1, methanol)

EXAMPLE 3

Preparation of the di-N-methylamide of (E)-2-(2-phenyl-ethenyl)-1,3-dioxolane-4(R),5(R)-dicarboxylic acid A mixture of the dimethylester of (E)-2-(2-phenyl-ethenyl)-1,3-dioxolane-4(R),5(R)-dicarboxylic acid (29.29 g; 0.1 mol) and a 33% (weight/weight) methanolic solution of methylamine (125 ml) is kept at room temperature for 1 hour. Evaporation of the solvent under vacuum leaves a residue which by crystallisation from an ethyl ether-methanol (100:1) mixture provides the di-N-methylamide of (E)-2-(2-phenyl-ethenyl)-1,3-dioxolane-4(R),5(R)-dicarboxylic acid (25 g; 0.07 moles; yield 70%). M.p. 114°-118° C.

$[\alpha]_D^{20}$=+53.67° (C=1, methanol)
$^1$H-NMR (90 MHz, acetone-$d_6$-TMS) delta (ppm); 2.70 (s, 1.5H); 2.73 (s, 1.5H); 2.76 (s, 1.5H); 2.80 (s, 1.5H); 2.90 (broad, NH, 2H); 4.66 (s, 2H); 5.63 (d, 1H, $J_{AB}$=6.6 Hz); 6.23 (dd, 1H, $J_{AB}$=6.6 Hz, $J_{BX}$=15.6 Hz); 6.90 (d, 1H, $J_{BX}$=15.6 Hz); 7.30-7.60 (m, 5H, aromatic protons).

I.R. (Nujol mull) $cm^{-1}$: 3330 (NH); 1650 (C=0); 1680 (C=0).

EXAMPLE 4

Preparation of the diamide of (E)-2-(2-phenyl-ethenyl)-1,3-dioxolane-4(R),5(R)-dicarboxylic acid A mixture of dimethylester of (E)-2-(2-phenyl-ethenyl)-1,3-dioxolane-4(R),5(R)-dicarboxylic acid (29.29 g; 0.1 mol) and a 30% aqueous solution of ammonium hydroxide (450 ml) is kept under stirring at room temperature for 12 hours. The reaction mixture is filtered, the precipitate washed with water and crystallized from methanol. In this manner, the diamide of (E)-2-(2-phenyl-ethenyl)-1,3-dioxolane-4(R),5(R)-dicarboxylic acid (15 g; 0.06 mol; yield 60%) is obtained. M.p. 161°–163° C.

$[\alpha]_D^{20} = +39.24°$ (C=1, methanol).

1H-NMR (90 MHz, acetone-d$_6$-TMS) delta (ppm); 2.83 (4H, NH); 4.67 (s, 2H); 5.67 (d, 1H, $J_{AB}=6.6$ Hz); 6.27 (dd, 1H, $J_{AB}=6.6$ Hz, $J_{BX}=15.6$ Hz); 6.87 (d, 1H, $J_{BX}=15.6$ Hz); 7.25–7.60 (m, 5H, aromatic protons).

I.R. (Nujol mull) cm$^{-1}$: 3330 (NH); 1650 (C=O); 1680 (C=O).

EXAMPLE 5

Preparation of the diamide of (E)-2-(2-phenyl-ethenyl)-1,3-dioxolane-4(R),5(R)-dicarboxylic acid A mixture of E-cinnamaldehyde (13.26 g; 0.1 mol), methanol (4.8 ml), trimethylorthoformate (12 ml; 11.6 g; 0.019 mol), dimethylester of 2(R),3(R)-dihydroxybutanedioic acid (21.3 g; 0.12 mol) and methanesulphonic acid (0.96 g; 0.01 mol) is kept at 40° C. and the low-boiling components distilled off under vacuum (about 14 mmHg). The reaction mixture is then poured into an aqueous 30% solution of ammonium hydroxide (100 ml). The mixture is kept under stirring at room temperature for 12 hours, filtered and the precipitate washed with water. Crystallization from methanol provides the diamide of (E)-2-(2-phenylethenyl)-1,3-dioxolane-4(R),5(R)-dicarboxylic acid (12 g; 0.46 mol; yield 46%). M.p. 161°–163° C.

$[\alpha]_D^{20} = +38.74°$ C. (C=1, methanol)

1H-NMR and IR spectral characteristics are identical to those of the product obtained as described in Example 4.

EXAMPLE 6

Preparation of the N-methylamide of 1(R)-6(S)-5(S)-bromo-4(S)-phenyl-3,7,9-trioxa-[4,2,1]-bicyclonan-2-one-8(R)-carboxylic acid

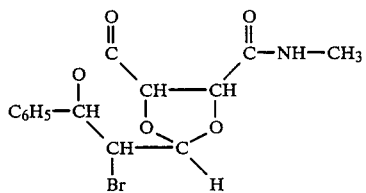

N-bromoacetamide (20 g; 145 mmol) is added under nitrogen at 15° C. to a mixture of di-N-methylamide of (E)-2-(2-phenyl-ethenyl)-1,3-dioxolane-4(R),5(R)-dicarboxylic acid (21.04 g; 72.5 mmol), acetonitrile (217 ml), and water (2.61 ml; 145 mmol).

The reaction mixture is kept under stirring at 15° C. for 23 hours, diluted with dichloromethane (500 ml) and washed with water (100 ml). The organic phase is then washed with a 2% sodium thiosulphate solution (2×100 ml), then with a saturated sodium chloride solution (100 ml) and dried with sodium sulphate.

Evaporation of the solvent under vacuum leaves a residue which by crystallisation form ethyl acetate provides the desired pure compound (18 g; 50.56 mmol, yield 70%). M.p. 114°–118° C.

$[\alpha]_D^{20} = -12.4°$ (C=1, ethyl acetate).

1H-NMR (300 MHz, DMSO-d$_6$) delta (ppm); 2.70 (s, 3H); 3.40 (s, 1H, NH); 4.90 (d, 1H, J=10.8 Hz); 5.04 (d, 1H, J=2.5 Hz) 5.55 (d, 1H, J=2.5 Hz) 5.73 (d, 1H, J=10.8 Hz); 6.24 (s, 1H); 7.4–7.5 (m, 5H, aromatic protons I.R. (chloroform) cm$^{-1}$: 3330, 1755, 1690 (C=O).

Elemental analysis; % found (% calculated); C 47.21 (47.21); H 3.98 (3.96); N 4.04 (3.93); Br 22.13 (22.44).

Mass (isobutane) m/e: 358 (10.8%); 356 (10.7%), 174 (100%).

EXAMPLE 7

Preparation of the N,N-dimethylamide of 1(R)-6(S)-5(S)-bromo-4(S)-phenyl-3,7,9-trioxa-[4,2,1]-bicyclonan-2-one-8(R)-carboxylic acid.

N-bromoacetamide (20 g; 145 mmoles) is added under nitrogen at 15° C. to a stirred mixture of di-N,N-dimethylamide of (E)-2-(2-phenylethenyl)-1,3-dioxolane-4(R),5(R)-dicarboxylic acid (23 g; 72.5 mmol), acetonitrile (217 ml) and water (2.61 ml; 145 mmol).

The reaction mixture is kept at 15° C. for 6 hours, diluted with dichloromethane (500 ml) and washed with water (100 ml). The organic phase is then washed with a 2% sodium thiosulphate solution (2×100 ml), then with a saturated sodium chloride solution and dried with sodium sulphate.

Evaporation of the solvent under vacuum leaves a residue (26.1 g) which by crystallization from acetone-water (7:5) provides the desired compound. M.p. 153°–4° C.

$[\alpha]_D^{20} = -82.66°$ (C=1, ethyl acetate).

1H-NMR (200 MHz, DMSO-d$_6$-TMS) delta (ppm): 2.86 (s, 3H); 3.08 (s, 3H); 4.83 (d, 1H, J=10.8 Hz); 5.34 (d, 1H, J=2.5 Hz); 5.72 (d, 1H, J=10.8 Hz); 5.98 (d, 1H, J=2.5 Hz); 6.10 (s, 1H); 7.357.54 (5H, aromatic protons).

I.R. (chloroform) cm$^{-1}$: 1735, 1660 (C=O).

Elemental, analysis; % found (% calculated): C 48.63 (48.66); H 4.37 (4.36); N 3.76 (3.78); Br 21.60 (21.59).

Mass (isobutane) m/e: 372 (8.55%), 370 (10.33%), 188 (13.88%), 133 (100%).

EXAMPLE 8

Preparation of the amide of 1(R)-6(S)-5-bromo-4-phenyl-3,7,9-trioxa-[4,2,1]-bicyclonan-2-one-8(R)-carboxylic acid.

N-bromoacetamide (17.36 g; 126 mmol) is added under nitrogen at 15° C. to a stirred mixture of the diamide of (E)-2-(2-phenyl-ethenyl)-1,3-dioxolane-4(R),5(R)-dicarboxylic acid (16.5 g; 62.9 mmoles) and dichloromethane (190 ml). The reaction mixture is kept at 15° C. for a further 24 hours, diluted with dichloromethane (200 ml), washed with water, then with a 2% sodium thiosulphate solution (2×100 ml), then with a saturated sodium chloride solution, and dried with sodium sulphate. Evaporation of the solvent under vacuum leaves the desired product. An analytically pure sample is obtained by silica gel chromatography (eluent dichloromethane: acetone=9:1); M.p. 187°–189° C.

$[\alpha]_D^{20} = -23.13°$ (C=1, ethyl acetate)

1H-NMR (200 MHz, DMSO-d$_6$-TMS) delta (ppm): 4.83 (d, 1H, J=10.9 Hz); 5.00 (d, 1H, J=2.5 Hz); 5.41 (d, 1H, J=2.5 Hz); 5.69 (d, 1H, J=10.9 Hz); 6.22 (s, 1H); 7.4–7.5 (5H, aromatic protons); 7.67 and 7.75 (broad band, 2H, NH).

I.R. (chloroform) cm$^{-1}$: 1740, 1660 (C=O); 3440.

Elemental analysis: % found (% calculated); C 45.51 (45.63); H 3.80 (3.53); N 4.55 (4.09); Br 23.21 (23.36).

Mass (isobutane) m/e: 344 (12.83%), 342 (15.74%), 160 (100%), 133 (15.45%).

EXAMPLE 9

Preparation of the amide of N-bromo-1(R)-6(S)-5(S)-bromo-4(S)-phenyl-3,7,9-trioxa-[4,2,1]-bicyclonan-2-imino-8(R)-carboxylic acid.

N-bromoacetamide (27.6 g; 0.2 mol) is added under nitrogen at 15° C. to a mixture of the diamide of (E)-2-(2-phenyl-ethenyl)-1,3-dioxolane-4(R),5(R)-dicarboxylic acid (26.27 g; 0.1 mol), acetonitrile (335 ml) and water (3.6 ml, 0.2 mol). The reaction mixture is kept at 15° C. for 5 hours, diluted with dichloromethane (700 ml), washed with water (100 ml), then with a 2% sodium thiosulphate solution (2×100 ml), then with a saturated sodium chloride solution, and dried with sodium sulphate. Evaporation of the solvent under vacuum leaves a residue (34 g) which by purification by silica gel chromatography provides the desired pure compound. M.p. 157° C.

$[\alpha]_D^{20} = -103.4°$ (C=1, ethyl acetate)

$^1$H-NMR (90 MHz, DMSO-d$_6$-TMS) delta (ppm): 4.83 (d, 1H, J=10.8 Hz); 5.31 (s, 2H); 5.73 (d, 1H, J=10.8 Hz); 6.16 (s, 1H); 7.3–7.6 (5H, aromatic protons); 7.66 (1H); 7.77 (1H). I.R. (KBr) cm$^{-1}$: 3460, 1680 (C=O); 1610 (C=N). Elemental analysis: % found (% calculated); C 37.60 (37.17); H 3.17 (2.88); N 6.25 (6.67); Br 37.98 (38.05). Mass (isobutane) m/e: 423 (54.68%), 421 (100%), 419 (48.14%), 343 (64.05%), 341 (69.89%), 239 (57%), 237 (61%), 160 (71.3%), 159 (88%), 133 (71%).

EXAMPLE 10

Preparation of the N,N-dimethylamide of 2(S)-/1(S)-bromo-2-(S)-hydroxy-2-phenylethyl/-1,3-dioxolane-4(R)-methoxycarbonyl-5(R)-carboxylic acid.

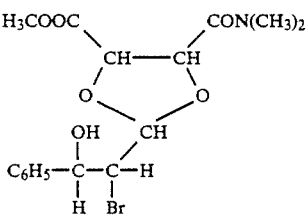

A solution of the N,N-dimethylamide of 1(R)6(S)-5(S)-bromo-4(S)-phenyl-3,7,9-trioxa-[4,2,1]-bicyclonan-2-one-8(R)-carboxylic acid (1 g; 2.7 mmol) in methanol (10 ml) is kept at reflux temperature for 2 hours.

Evaporation of the solvent under vacuum leaves the desired pure compound (1.03 g; 2.673 mmol; yield 99%) in the form of an oil.

$^1$H-NMR (200 MHz, CDCl$_3$-TMS) delta (ppm); 2.93 (s, 3H); 3.10 (s, 3H); 3.40 (1H, OH); 3.80 (s, 3H); 4.36 (dd, 1H, J$_{AB}$=7.8 Hz, J$_{AX}$=3.3 Hz); 5.06 (d, 1H, J$_{AB}$=7.8 Hz); 5.16 (ABq, J=4.2 Hz, Δv=5.77 Hz); 5.43 (d, 1H, J$_{AX}$=3.3 Hz); 7.1–7.3 (5H, aromatic protons).

I.R. (chloroformi) cm$^{-1}$; 3500 (OH); 1740, 1660 (C=O).

EXAMPLE 11

Preparation of the N,N-dimethylamide of 2(S)-[1(S)-bromo-2(S)-hydroxy-2-phenylethyl]-1,3-dioxolane-4(R)-ethoxycarbonyl-5(R)-carboxylic acid.

Operating in a manner analogous to that described in the preceding example but using ethanol, the desired pure product is obtained with a yield of 98%. M.p. 154°–156° C.

$[\alpha]_D^{20} = -18.3°$ (C=1%, ethyl acetate)

$^1$H-NMR (90 MHz, acetone-d$_6$-TMS) delta (ppm): 1.26 (t, 3H, J=7.2 Hz); 2.73 (s, 1H, OH); 2.93 (s, 3H); 3.10 (s, 3H); 4.20 (q, 2H, J=7.2 Hz); 4.43 (dd, 1H, J$_{AB}$=11.4 Hz, J$_{BX}$=4.8 Hz); 4.96 (ABq, 2H, J=4.2 Hz, Δv=17.5 Hz); 5.33 (d, 1H, J$_{AB}$=11.4 Hz); 5.40 (d, 1H, J$_{BX}$=4.8 Hz); 7.2–7.5 (5H, aromatic protons).

I.R. (chloroform) cm$^{-1}$: 3500 (OH); 1740, 1660 (C=O).

Elementary analysis: % found (% calculated); C 49.22 (49.05); H 5.26 (5.33); N 3.52 (3.37); Br 19.18 (19.20).

Mass (isobutane) m/e: 418 (51.7%), 416 (51.89%), 216 (100%).

X-Ray analysis confirmed the assigned structure.

EXAMPLE 12

Preparation of N,N,N',N'-tetramethylamide of 2-ethenyl-1,3-dioxolane-4(R),5(R)-dicarboxylic acid.

A mixture of Acrolein diethyl acetal (13 g; 0.1 mol), (2R, 3R)-(+)-N,N,N',N'-tetramethyl-2,3-dihydroxy-butanedioicamide (20.4 g; 0.1 mol), benzene (100 ml), and camphorsulfonic acid (1.17 g, 0.005 mol) is kept at reflux for 30 minutes.

The reaction mixture is cooled spontaneously to room temperature and then treated with anhydrous sodium carbonate (0.53 g, 0.005 mol) The mixture is filtered and the solvent evaporated to give a crude which is purified by distillation: N,N,N',N',-tetramethylamide of 2-ethenyl-1,3-dioxolane-4(R),5(R)-dicarboxylic acid. (1.3 g; 0.054 mol; 53.7% yield)

B.P. =147°–151° C./0.3 mmHg.

$[\alpha]_D^{21} = -28.53$ (C=2.43/CHCl$_3$)

$^1$H-NMR (300 MHz DMSO-TMS) delta (ppm): 2.84 (s, 3H); 2.845 (s, 3H); 3.0 (s, 3H); 3.05 (s, 3H); 5.15 (AB, sistem 2H, J$_{AB}$=5 Hz); 5.38 (dd 1H, J$_{gem}$=1.5, J=10.5 Hz); 5.43 (d, 1H, J=6 Hz); 5.51 (dd, 1H, J$_{gem}$=1.5 Hz, J=17 Hz); 5.78 (m, 1H, J=10.5 Hz, J=6 Hz, J=17 Hz).

IR 2% CHCl$_3$ cm$^{-1}$ 1650 (C=O).

EXAMPLE 13

Preparation of N,N-dimethylamide of 1-(R)-4-Bromo-methyl-3,6,8-trioxa-[3,2,1]-bicyclooctan-2-one-7(R)-carboxylic acid.

N-bromoacetamide (3.39 g, 0.0246 mol) is added under nitrogen at 15° C. to a stirred mixture of the N,N,N',N',-tetramethylamide of 2-ethenyl-1,3-dioxolane-4(R),5(R)-dicarboxylic acid (3 g, 0.0124 mol), acetonitrile (37 ml) and water (443 μl; 0.0246 mol).

The reaction mixture is kept under stirring at 15° C. for 15 hours, diluted with dichloromethane (70 ml) and washed with buffered (pH 7) aqueous solution.

The organic phase is then washed with 2% sodium thiosulphate solution and dried with sodium sulphate.

Evaporation of the solvent under vacuum leaves a residue which by crystallization from dichloromethane provides the desired bromolactones as pure epimer (1.5 g; 0.0051 mol; 41% yield)

M.p. =198°–203° C.

$[\alpha]_D^{20} = -46°$ (c=1/DMSO).

$^1$H-NMR (300 MHz DMSO-TMS) delta (ppm): 2.84 (s, 3H); 3.02 (s, 3H); 3.7 (AB part of ABX, system 2H, J$_{AB}$=11 Hz, J$_{BX}$=8.4 Hz, J$_{AX}$=4.5 Hz); 4.78 (X part of ABX, system 1H, J$_{AX}$=4.5 Hz, J$_{BX}$=8.4 Hz, J=2.2

Hz); 5.27 (broad singlet 1H); 5.34 (broad singlet, 1H); 5.98 (d, 1H, J=2.2 Hz).

$C_{13}$ NMR (300 MHz DMSO) delta (ppm). 29.6 ($CH_2Br$); 35.257, 35.39

98.209

165.25 (C=0); 165.58 (C=0).
IR ($CHCl_3$) $cm^{-1}$: 1770, 1650 (C=0).

EXAMPLE 14

Preparation of N,N,N',N'-tetramethylamido of (E)-2(1-propenyl)-1,3-dioxolane-4(R),5(R) dicarboxylic acid.

A mixture of E-crotonaldehyde diethyl acetal (14.3 g, 0.1 moles), 2R, SR-(+) N,N,N',N'-tetramethyl-2,3-dihydroxi-butanedioicamide (20.4 g, 0.1 mol) benzene (100 ml), and camphorsulfonic acid (1.17 g, 0.005 mol) is kept at reflux for 30 minutes.

The reaction mixture is cooled spontaneously to room temperature, and added with 0.53 g, 0.005 mol anhydrous sodium carbonated. The mixture is filtrated and the solvent evaporated to give a crude which is purified by distillation B.P.=168°-169° C. 0.5 mmHg (13 g, 0.054 mol; 54% yield).

$[\alpha]_D^{20} = -27.2$ (C=1/$CHCl_3$).

$^1$H-NMR (300 MHz DMSO-TMS) delta (ppm); 1.7 (dd, 3H, J=7 Hz, J=2 Hz); 2.85 (s, 3H); 2.86 (s, 3H); 3.01 (s, 3H); 3.07 (s, 3H); 5.13 (AB, system 2H, $J_{AB}$=5.2 Hz); 5.40 (d, 1H, J=7 Hz); 5.44 (m, 1H, J=14.6 Hz, J=7 Hz, J=2 Hz); 5.97 (m, 1H, J=14.6 Hz, J=7 Hz).

IR 2% $CHCl_3$ $cm^{-1}$ 1650 (C=0).

EXAMPLE 15

Reaction of N,N,N',N'-tetramethylamide of -2(1-propenyl)-1,3-dioxolane-4(R),5(R)-dicarboxylic acid with N-bromoacetamide.

N-bromoacetamide (3.39 g; 0.0246 mol) is added under nitrogen at 15° C. to a mixture of the N,N,N',N'-tetramethylamide of -2(1-propenyl)-1,3-dioxolane-4(R),5(R)-dicarboxylic acid (3.15 g; 0.0123 mol), acetonitrile (37 ml) and water (443 μl; 0.0246 mol).

The reaction mixture is kept at 15° C. per 4 hours, diluted with dichloromethane (70 ml) and washed with buffered solution at pH 7. The organic phase is then washed with 2% sodium thiosulphate solution and dried with sodium sulphate.

Evaporation of the solvent under vacuum leaves a residue (1.6 g) containing mainly the bromolactones.

The major stereoisomer is characterized by $^1$H NMR.

$^1$H-NMR (300 MHz DMSO-TMS) delta (ppm): 1.56 (d, 3H, J=6.4 Hz); 2.86 (s, 3H); 3.05 (s, 3H); 4.3 (dd, J=20 Hz, J=1 Hz); 4.89 (dq, 1H, H=10 Hz, J=6.4 Hz); 5.26 (d, 1H, J=3 Hz); 55.77 (d, 1H, J=3 Hz); 5.9 (d, 1H, J=1 Hz);

IR 2% $CHCl_3$ $cm^{-1}$: 1750, 1650 (C=0).
We claim:

1. A stereoselective process for preparing optically active alpha,beta-difunctionalised carbonyl compounds which comprises
   (a) reacting an alpha,beta-unsaturated aldehyde or ketone of formula

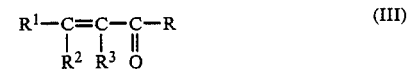

wherein

R represents a hydrogen atom; a $C_1$-$C_4$ alkyl group optionally substituted with from one to three substituents chosen from halogen atoms, hydroxy, nitro, cyano, $C_1$-$C_4$ alkoxy or or $C_3$-$C_6$ cycloalkyl groups, phenyl, naphtyl, pyridyl, furyl or thienyl which can themselves be substituted with halogen atoms, $C_1$-$C_4$ alkyl or alkoxy groups; a benzyl or a phenyl group optionally substituted with from one to three substituents chosen from halogen atoms, hydroxy, nitro, cyano, $C_1$-$C_4$ alkyl, $C_1$-$C_4$ alkylthio, $C_1$-$C_4$ alkoxy, $C_1$-$C_4$ acyloxy, $C_1$-$C_4$ haloalkyl or $C_1$-$C_4$ haloalkoxy groups;

$R^1$, $R^2$ and $R^3$, which can be the same or different, represent a hydrogen atom; a $C_1$-$C_4$ alkyl group optionally substituted with from one to three substituents chosen from halogen atoms, hydroxy, nitro, cyano, $C_1$-$C_4$ alkoxy or or $C_3$-$C_6$ cycloalkyl groups, phenyl, naphtyl, pyridyl, furyl or thienyl which can themselves be substituted with halogen atoms, $C_1$-$C_4$ alkyl or alkoxy groups; an aryl group chosen from furyl, thienyl, pyrrolyl, phenyl, pyridyl, naphtyl, quinolyl or diphenyl, said groups being optionally substituted with from one to three substituents chosen from halogen atoms, hydroxy, nitro, cyano, $C_1$-$C_4$ alkyl, $C_1$-$C_4$ alkylthio, $C_1$-$C_4$ alkoxy, $C_1$-$C_4$ acyloxy, $C_1$-$C_4$ haloalkyl or $C_1$-$C_4$ haloalkoxy groups; with L(+) tartaric acid or D(−) tartaric acid or a derivative thereof of formula $R^4$—CO—CH(OH)—CH(OH)—CO—$R^5$ wherein $R^4$ and $R^5$, which can be the same or different, represent hydroxy, $C_1$-$C_4$ alkoxy or an amino group mono- or di-substituted with $C_1$-$C_4$ alkyl, 1-pyrrolidyl or 1-piperidyl group, or an O$^-$M$^+$ group where M$^+$ represents the cation of an alkaline metal; in an inert solvent, in the presence of an acid catalyst at a temperature of from room up to reflux temperature, for a period of time of from 2 to 20 hours, by eliminating the reaction water by means of a dehydrating agent or by azeotropic distillation;

(b) halogenating the obtained ketal of formula

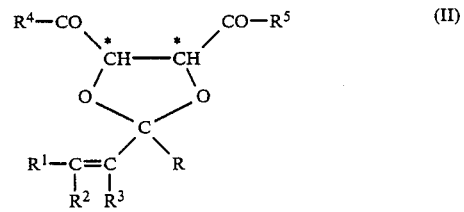

in which R, $R^1$, $R^2$, $R^3$, $R^4$ and $R^5$ have the same meanings as above, at a temperature of from −10°

C. to 20° C., for a period of time of from 1 to 48 hours, in a solvent chosen from halogenated hydrocarbon, acetonitrile, ethyl ether, amides, aliphatic alcohols, tetrahydrofuran, dioxane, water or their mixtures, by means of an halogenating agent chosen from chlorine, bromine, iodine, iodine chloride, tetra-alkylammonium or tetra-alkylphosphonium perhalides, N-bromo-succinimide, N-bromo-acetamide, N-chloro succinimide, N-iodo-succinimide, N-halo-amines, cupric bromide, hexachloro-cyclohexadienone;

(c) hydrolysing the obtained compound of formula

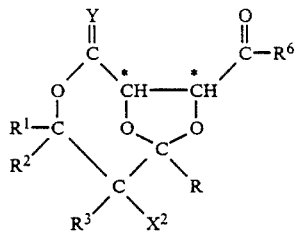
(IVa)

or

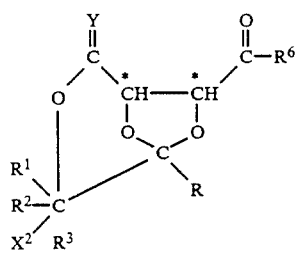
(IVb)

in which

R, $R^1$, $R^2$, $R^3$, $R^4$ have the same meanings as above and $R^6$ has the meanings given for $R^4$, or is a $-N(X^2R^1)$;

$X^2$ represents a chlorine, bromine or iodine atom;

Y represents an oxygen atom or an $=N-R^7$ group in which $R^7$ represents a hydrogen, chlorine, bromine or iodine atom, a $C_1$-$C_4$ alkyl, or a phenyl;

at a temperature of from room temperature to 100° C. in an alcoholic or aqueous/alcoholic medium, for a period of time of from 2 to 20 hours, to an aldehyde or to a ketone of formula

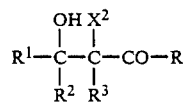
(Ia)

or

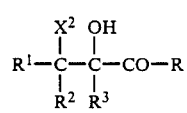
(Ib)

in which R, $R^1$, $R^2$, $R^3$, and $X^2$ have the same meanings as above.

2. A process as claimed in 1, in which the dehydrating agent of the stage (a) is a trialkylorthoformate.

3. A process as claimed in 1, in which the acid catalyst of the stage (a) is the methanesulfonic acid.

4. A process as claimed in 1, wherein the halogenating agent of the stage (b) is N-bromoacetamide and the solvent is a mixture of acetonitrile and water.

5. A process as claimed in 1, in which the hydrolysis of the stage (c) is runned out in the presence of an acid catalyst.

* * * * *